US006698886B2

(12) United States Patent
Pollack et al.

(10) Patent No.: US 6,698,886 B2
(45) Date of Patent: Mar. 2, 2004

(54) IRIDOTOMY AND TRABECULOPLASTY GONIOLASER LENS

(75) Inventors: Irvin P. Pollack, Baltimore, MD (US); Daniel M. Bell, Seattle, WA (US); Raymond D. Graham, Renton, WA (US); Peter G. Harrington, Seattle, WA (US)

(73) Assignee: Ocular Instruments, Inc., Bellevue, WA (US)

( * ) Notice: Subject to any disclaimer, the term of this patent is extended or adjusted under 35 U.S.C. 154(b) by 125 days.

(21) Appl. No.: 10/126,478

(22) Filed: Apr. 18, 2002

(65) Prior Publication Data

US 2002/0167644 A1 Nov. 14, 2002

Related U.S. Application Data

(60) Provisional application No. 60/286,210, filed on Apr. 24, 2001.

(51) Int. Cl.[7] ............................... A61B 3/00; A61B 3/10
(52) U.S. Cl. ....................................... 351/219; 351/221
(58) Field of Search ................................ 351/205, 219, 351/221, 246, 247, 160 H, 160 R; 606/4, 6, 18

(56) References Cited

U.S. PATENT DOCUMENTS

| 4,350,163 A | 9/1982 | Ford, Jr. et al. |
| 4,391,275 A | 7/1983 | Fankhauser et al. |
| 4,409,979 A | 10/1983 | Roussel et al. |
| 4,506,962 A | 3/1985 | Roussel |
| 4,558,698 A | 12/1985 | O'Dell |
| 4,598,984 A | 7/1986 | Rol |
| 4,907,872 A | 3/1990 | Schirmer et al. |
| 5,359,372 A | 10/1994 | Kida et al. |
| 5,479,222 A | * 12/1995 | Volk .............................. 351/219 |
| 5,548,352 A | 8/1996 | Dewey |
| 5,784,147 A | * 7/1998 | Volk .............................. 351/219 |

OTHER PUBLICATIONS

*American Journal of Ophthalmology* 91(5):678–681.
Direct View & Gonioscopy Lenses, Volk Optical Inc., advertisement.
March, M.D., Wayne F., et al., "Improved Goniolens for YAG Sclerostomy," *Ophthalmic Surgery*, p. 513.
*Ocular Instruments 2001 Product Catalog*, 2001, pp. 7,9, 10,15,17.

* cited by examiner

Primary Examiner—Brian L. Casler
Assistant Examiner—John R. Sanders
(74) *Attorney, Agent, or Firm*—Christensen O'Connor Johnson Kindness PLLC

(57) ABSTRACT

An iridotomy and trabeculoplasty goniolaser lens has a contact lens element, a planar mirror offset from the optical axis of the contact lens element and first and second button lenses mounted on the anterior surface of the contact lens element. Magnification, curvature and location of the button lenses are chosen so as to provide the ability to simultaneously deliver laser energy to the iris of a patient's eye along a first optical path offset from the optical axis of the contact lens element and to view the trabecular meshwork around the region where the laser energy was applied. This ability eliminates the need for a plurality of contact lenses for delivering energy and viewing the eye and further eliminating the need for refocusing the microscope through which the surgeon views the eye.

8 Claims, 2 Drawing Sheets

IRIDOTOMY AND TRABECULOPLASTY GONIOLASER LENS

CROSS-REFERENCE TO RELATED APPLICATION

This application claims the benefit of U.S. Provisional Application No. 60/286,210, filed Apr. 24, 2001.

FIELD OF THE INVENTION

The present invention relates to contact lenses used by ophthalmologists for diagnosis and laser surgery of the eye, and more particularly to an iridotomy and trabeculoplasty goniolaser lens.

BACKGROUND OF THE INVENTION

Glaucoma is an eye disease that can lead to blindness if not properly treated. Elevated intraocular pressure is frequently an early sign of the disease. Reduction of the intraocular pressure may prevent loss of vision. The goniolaser lens may be designed to focus the laser light to treat two specific types of glaucoma.

Angle-closure glaucoma: In angle-closure glaucoma the intraocular fluids (aqueous humor) must pass through the pupil from behind the iris (posterior chamber) to a position in from of the iris (anterior chamber). The aqueous humor then escapes from the eye through microscopic channels located at the angle of the anterior chamber between the peripheral iris and cornea. In angle-closure glaucoma there occurs a block at the pupil so that the aqueous humor cannot pass from the posterior to the anterior chamber and the eye pressure becomes very elevated.

One method developed for relief of intraocular pressure caused by angle-closure glaucoma is to perform an iridotomy using laser ablation surgery. This surgical procedure is accomplished by positioning an appropriately configured contact lens on the cornea of an eye and delivering laser energy to the iris. The laser energy is focused on the peripheral iris to generate an opening through the iris. Intraocular fluid (aqueous humor) can then bypass the blocked pupil and move through the newly created iris opening from the posterior to the anterior chamber. This allows the aqueous humor to reach the outflow channels in the anterior chamber angle and relieve the pressure and symptoms of closed angle glaucoma.

Open-angle glaucoma: Open-angle glaucoma is caused by an abnormality in the microscopic channels, trabecular meshwork, that are located in the angle of the anterior chamber. Eyedrop medications may help the aqueous humor to pass through the meshwork, but not in all cases.

Another method for relieving the symptoms of open-angle glaucoma is to perform trabeculoplasty using laser ablation surgery. This procedure is accomplished by delivering laser energy to the trabecular meshwork to allow better passage of the aqueous humor through it. One theory suggests that the laser alters the intracellular and intercellular structures in the trabecular meshwork and allows the fluids to pass through with less obstruction.

Prior contact lenses employed for these purposes work efficiently for the application of laser energy to the eye. However, viewing the trabecular meshwork before and after an iridotomy procedure has necessitated removal of the laser lens and substitution of another viewing lens. While attempts have been made at combining a laser delivery lens and a viewing lens, the attempted combinations have not been successful for a variety of reasons. The major reason for lack of success has been the necessity to completely refocus the binocular microscope through which the surgeon is manipulating the laser energy and through which the surgeon views the trabecular meshwork.

During an iridotomy procedure, it is desirable to view the trabecular meshwork immediately after the delivery of laser energy to determine the efficacy of the procedure. If the aperture through the iris has been successfully completed, fluid pressure in the posterior chamber will be relieved and will allow the iris to flatten to its natural state rather than the anteriorly bowed configuration that occurs in the presence of excessive intraocular pressure in the posterior chamber. When laser iridotomy has been mechanically successful, the anterior chamber angle will open, as observed through the gonioscopy portion of the lens. However, if it is observed that the angle failed to open, then additional application of laser energy may be required. Thus, if the anterior chamber angle and trabecular meshwork could be viewed immediately after the initial delivery of laser energy through the same contact lens, an additional application of laser energy could be applied to the same or another location without removing the laser delivery lens, without substituting the viewing lens and without once again repositioning the laser delivery lens.

SUMMARY OF THE INVENTION

In accordance with the present invention, an iridotomy goniolaser lens is provided through which laser energy can be delivered to the eye and through which the treated area can be observed. In a currently preferred embodiment, the lens comprises four elements: a contact lens, a planar mirror, a first button lens, and a second button lens. The contact lens has an optical axis, a concave posterior contact surface, and an anterior planar surface. The contact lens element has an angled surface offset from its optical axis. The angled surface is planar and extends laterally and anteriorly from a location radially offset from the optical axis of the contact lens element and adjacent to the concave contact lens surface but anterior thereof. The surface forms an internally reflective planar mirror. The first button lens has a planar posterior surface and a convex anterior surface. The planar surface of the first button lens is in optical contact with the planar surface of the contact lens element and is offset from the optical axis of the contact lens element in a direction opposite from the offset of the angled surface. The magnification, curvature, and location of the first button lens is chosen to provide a virtual image in a first image plane of a predetermined location on the iris of a patient when the contact lens surface of the contact lens element is in optical contact with the cornea of the eye of the patient. The second button lens has a planar posterior surface and a convex anterior surface. The planar surface of the second button lens is in optical contact with the planar surface of the contact lens element. The second button lens is offset from the optical axis of the contact lens in the direction of the offset of the angled mirror surface and is positioned over the angled mirror surface. The magnification, curvature, and location of the second button lens is chosen to provide a virtual image in a second image plane of the trabecular meshwork of the eye of the patient when the surface of the contact lens element is in optical contact with the cornea of the eye of the patient. The magnification, curvature, and location of the first and second button lens are preferably chosen such that an optical microscope can be focused on the first and second image planes with little or no focus adjustment, thus allowing delivery of laser energy to the iris and viewing of the trabecular meshwork through the same lens.

The same lens can be employed for trabeculoplasty. For this procedure, laser energy is directed toward the angled mirror surface and reflected to the trabecular meshwork. The results of the trabeculoplasty can be viewed along the same optical path.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 2:
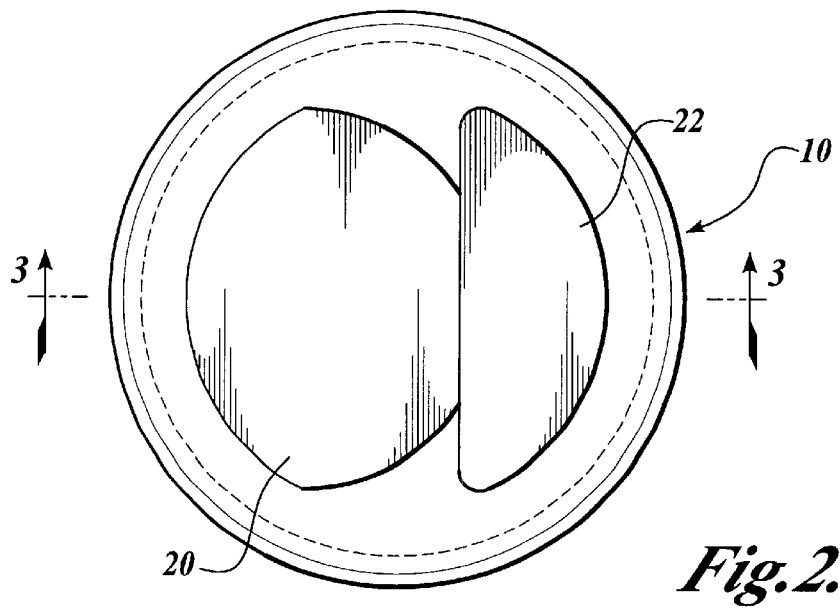
FIG. 1 and FIG. 2 are respective elevation and top views of a contact lens constructed in accordance with the present invention.
Figure 1:
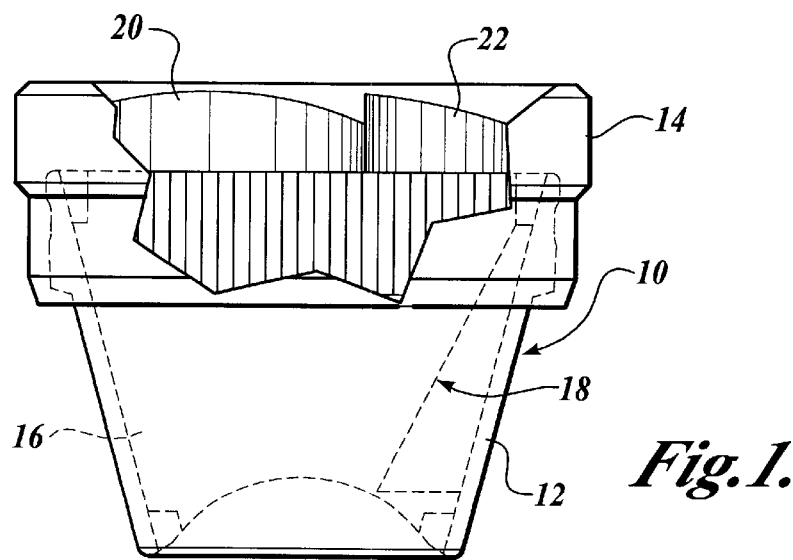

Referring now to FIGS. 1 and 2, a preferred embodiment of the laser surgery lens 10 of the present invention is housed in a holder comprising a lower frustoconically shaped shell 12 and an upper retaining ring 14. Housed within the holder is a contact lens element 16, a mirror 18, and first and second button lenses 20 and 22, respectively.

Figure 3:
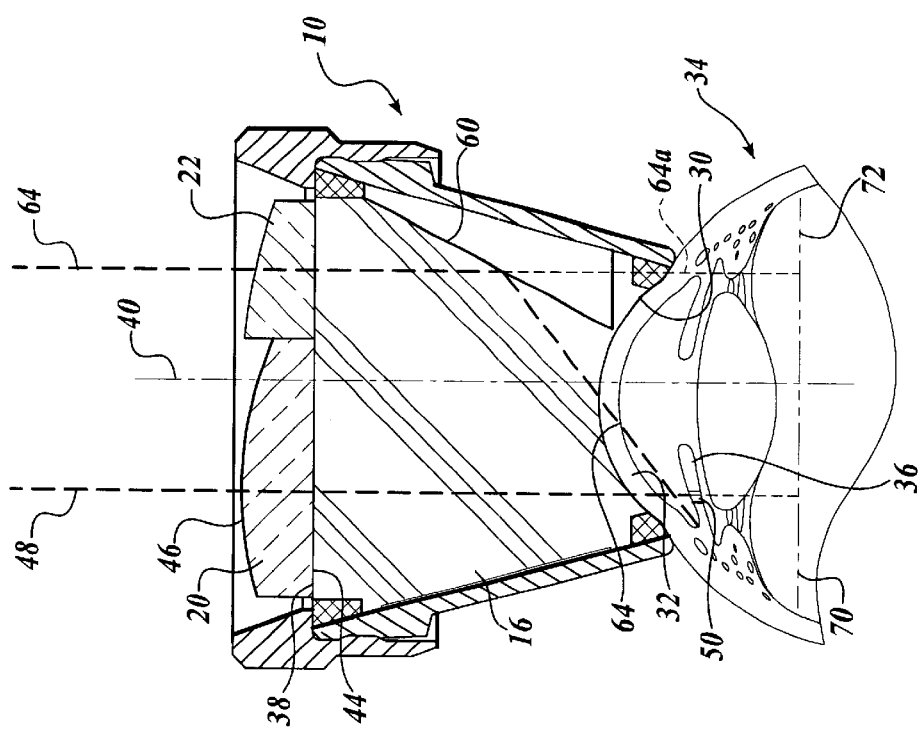
FIG. 3 is a longitudinal sectional view of the lens along section line 3—3 of FIG. 2 shown in contact with the cornea of a patient's eye and illustrating the optical path for the delivery of laser energy.

Referring now to FIG. 3, the contact lens element 16 has a concave posterior surface 30 that has a curvature that approximates the curvature of the cornea 32 of an eye 34 of a patient. The iris 36 of the eye is shown in an anteriorly distended position that is typically symptomatic of closed angle glaucoma. It is the purpose of iridotomy surgery to relieve the intraocular pressure on the iris so that it can relax to its normal position (shown in FIG. 4). The anterior surface 38 of the contact lens element is planar and is oriented perpendicularly to the optical axis 40 of the contact lens element 16. When the contact lens 10 is positioned on the patient's eye 34, the optical axis 40 is also positioned generally along the optical axis of the eye.

The first button lens 20 has a planar posterior surface 44 and a convex anterior surface 46. The planar posterior surface of the first button lens 20 is placed in optical contact with the anterior planar surface 44 of the contact lens element 16. By optical contact it is meant either direct surface-to-surface contact or contact with an optical glue or other bridging material that minimizes refraction and reflection otherwise caused at the junction of two optical surfaces. The first button lens 20 is offset laterally in a first direction from the optical axis 40 of the lens. The lateral positioning of the button lens 20 as well as its curvature and magnification are chosen such that laser energy can be delivered along the site line 48 parallel to the optical axis 40, through the cornea 32 and onto the iris. The lens is designed to focus the laser energy on the iris so that the heat generated will ablate the tissue of the iris and create an aperture or hole 50 through the iris. One of ordinary skill will recognize that the anterior surface of the first button lens 20 may be spheric, aspheric, diffractive, or a combination thereof depending upon the particular design and material parameters chosen.

The contact lens element 16 also has a planar surface 60 that is offset in the opposite direction from the offset of the first button lens 20. The lower edge of the planar surface 60 is positioned above but adjacent the contact lens surface 30. The planar surface 60 extends laterally and anteriorly from that position to a location near the upper planar surface 38. This planar surface 60 functions as mirror 18 to reflect light rays internal to the lens in a manner as discussed below. If desired, a reflective coating can be applied to the surface 60. Alternately, a mirror element having a planar mirrored surface may be positioned in optical contact with the planar surface 60 on the contact lens element.

The second button lens 22 is offset from the optical axis 40 in the same direction as the planar surface 60. The curvature, magnification and location of the second button lens 22 are chosen so as to provide a sight path 64 that extends from anterior to the button lens 22 along a path that is first parallel to the optical axis 40 of the composite lens and is then reflected by the surface of the mirror 18 formed by surface 60 at an angle that allows the trabecular meshwork adjacent and around the aperture 50 to be viewed by the ophthalmologist performing the surgery. The angle of the surface 60 and of course, the mirror 18 are chosen so as to provide the appropriate sight path 64. One of ordinary skill will recognize that the anterior surface of the second button lens 22 may be spheric, aspheric, diffractive, or a combination thereof depending upon the particular design and material parameters chosen.

The combination of the button lens 20 and the contact lens element creates a virtual image at a virtual image plane 70, which lies within the eye. Similarly, the combination of the button lens 22 mirror and contact lens element forms a second virtual image of the trabecular meshwork at a virtual image plane 72, which is also within the eye. In accordance with the present invention, the power and curvature of the respective button lenses 20 and 22 are chosen so that the virtual images 70 and 72 are preferably simultaneously in focus to the user of the lens 10. That is, the virtual image formed along sight path 48 and the image formed along sight path 64 and 64a preferably lie in substantially the same plane. This allows the ophthalmologist performing the laser surgery to focus the binocular microscope in a single plane so that both the laser energy can be focused at the base of the iris 36 and the trabecular meshwork can be viewed simultaneously or serially without moving or replacing the contact lens element and without the need to substantially refocus of the binocular microscope.

While it is most preferred that the images 70 and 72 lie substantially in the same plane, one of ordinary skill will readily understand that the visual images may be separated by a small distance which may require only slight refocusing of the binocular microscope through which the surgeon normally views the images. A separation of the images 70 and 72 by 5 mm is quite acceptable, requiring little refocusing during a procedure.

Figure 4:
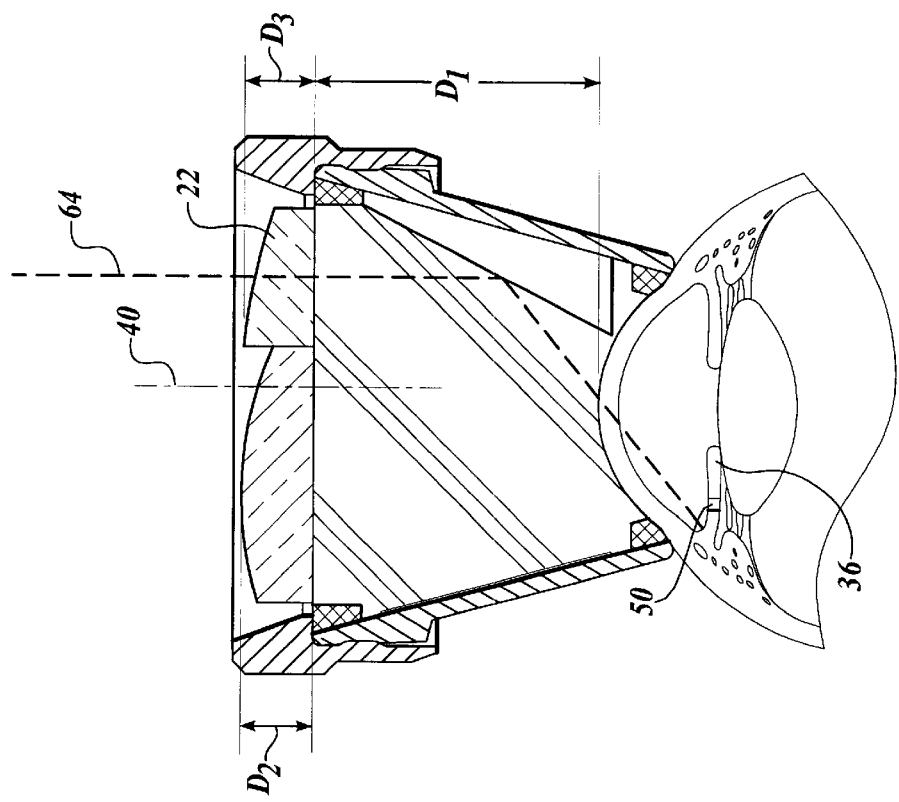
FIG. 4 is a view similar to FIG. 3 after laser energy has been delivered and showing the optical path for viewing the trabecular meshwork.

As shown in FIG. 4, the aperture 50 has been successfully created. When the trabecular meshwork is viewed along optical path 64, it is clear to the surgeon that the iris 36 has relaxed to its natural position because intraocular fluid has been allowed to escape from the posterior chamber into the anterior chamber through aperture 50.

The lens of the present invention can also be used to treat open angle glaucoma with trabeculoplasty. In this procedure, the trabecular meshwork is viewed along the sight path indicated by dashed line 64 using the internally reflective surface 60. In this procedure, however, the laser energy is also delivered along the same path to ablate or burn the trabecular meshwork to render it perforate to intraocular fluid. After surgery, the meshwork can again be viewed along path 64.

In a preferred embodiment, the curvature of the contact lens surface 30 is defined by a radius of curvature ($R_1$) equal to 7.4 mm and distance D1 is 14.4 mm. The curvature of the anterior surface of button lens 20 is defined by a radius of curvature ($R_2$) equal to 18.6 mm. The optical axis of the button lens 20 is offset by 4.5 mm from the optical axis 40 of the composite lens. The thickness D2 is 2.5 mm. The second button lens 22 has a thickness D3 of 2.5 mm. The curvature of the anterior surface of the button lens 22 is defined by a radius of curvature ($R_3$) equal to 31.0 mm. The optical axis of the button lens 22 is coincident with the optical axis 40 of the contact lens. The mirrored surface 60 forming mirror 18 is set at an angle of 28 degrees relative to the optical axis 40 of the composite lens. One of ordinary skill will readily recognize that the powers of the lens so defined, the angles of the mirror and other pertinent parameters can be changed so long as the functionality provided by the present invention is retained.

One of ordinary skill will also recognize that the individual lens elements comprising the preferred embodiment of the lens of the present invention may be created in one or more multifunctional elements. It is possible, for example, albeit more expensive to machine the equivalent of the button lenses from the same optical element as the contact lens. Moreover, if separate elements are employed, the surfaces between the elements such as surfaces 38 and 44 may not only be planar, as is preferred, but spherical or aspherical as desired.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A laser lens for use in laser surgery on an eye of a patient comprising:

a contact lens portion having an optical axis, a concave posterior contact surface and an anterior surface, said contact lens portion having a mirror associated therewith and offset from the optical axis thereof, the mirror having an angled surface that is planar and that extends from a location laterally offset from both the optical axis of the contact lens element and the concave contact lens surface, a first button lens portion having an anterior surface, said first button lens being in optical association with said contact lens element and being laterally offset from the optical axis of said contact lens element in a direction opposite from the offset of said angled surface, a second button lens portion having an anterior surface, said second button lens being in optical association with said contact lens element, said second button lens portion being laterally offset from the optical axis of the contact lens element and being positioned over said mirror, the magnification, curvature, and location of said first button lens portion being chosen to provide a virtual image in a first image plane of a predetermined location of the iris of the patient when the contact lens surface of the contact lens element is in optical contact with the cornea of the eye of the patient, and the magnification, curvature, and location of the second button lens portion being chosen to provide a virtual image in a second image plane of the trabecular meshwork of the eye of the patient when the surface of the contact lens element is in optical contact with the cornea of an eye of the patient, the first and second image planes being positioned relative to each other such that an optical microscope can be focused on the first and second image planes.

2. The laser lens of claim 1 wherein:

said first button lens portion is a separate element having a posterior surface in optical contact with the anterior surface of said contact lens.

3. The laser lens of claim 1 wherein:

said second button lens portion is a separate element having a posterior surface in optical contact with the anterior surface of said contact lens.

4. The laser lens of claim 3 where:

said first button lens portion is a separate element having a posterior surface in optical contact with the anterior surface of said contact lens.

5. The laser lens of claim 4 wherein said anterior surface of said contact lens and said posterior surfaces of said button lenses are planar.

6. The laser lens of claim 5 wherein the magnification, curvature and location of said button lenses are chosen so that said first and second image planes are substantially coplanar so that an optical microscope can be simultaneously focused on said image planes.

7. The laser lens of claim 1 wherein said mirror is formed by an angled surface integral with said contact lens portion.

8. The laser lens of claim 1 wherein said angled surface has a reflective coating thereon.

* * * * *